United States Patent [19]
Runckel

[11] Patent Number: 5,815,235
[45] Date of Patent: Sep. 29, 1998

[54] SKI GOGGLES WITH PIVOTAL FRAME MEMBERS FOR INTERCHANGING LENSES

[75] Inventor: John L. Runckel, Lake Oswego, Oreg.

[73] Assignee: John L. Runckel Trust, Portland, Oreg.

[21] Appl. No.: 890,223

[22] Filed: Jul. 9, 1997

[51] Int. Cl.$^6$ ............................... G02C 1/08; G02C 1/00
[52] U.S. Cl. ................................ 351/92; 351/86; 351/90
[58] Field of Search ................................. 351/86, 83, 90, 351/91, 92, 41, 44; 2/441

[56] References Cited

U.S. PATENT DOCUMENTS

| | | |
|---|---|---|
| 1,208,410 | 12/1916 | Van Tassel . |
| 1,720,814 | 7/1929 | Baker . |
| 2,364,584 | 12/1944 | Malcom . |
| 3,229,303 | 1/1966 | Jonassen . |
| 4,268,130 | 5/1981 | Vinocur . |
| 4,730,915 | 3/1988 | Jannard . |
| 5,227,817 | 7/1993 | Simioni ..................................... 351/80 |
| 5,373,331 | 12/1994 | Vallalla et al. . |
| 5,423,092 | 6/1995 | Kawai ..................................... 351/44 |

FOREIGN PATENT DOCUMENTS

| | | |
|---|---|---|
| 576971 | of 1924 | France . |
| 24 19 490 | 10/1975 | Germany . |

*Primary Examiner*—Hung X. Dang
*Attorney, Agent, or Firm*—Kolisch, Hartwell, Dickinson, McCormack & Heuser

[57] ABSTRACT

A pair of ski goggles is disclosed which has unitary upper and lower frame members that are each configured to extend substantially between a user's temples, and each include a pair of end regions. The upper and the lower frame members collectively define an aperture into which a lens is removably received, and the goggles further includes a pair of connectors. Each connector couples a respective one of the end regions on the upper frame member to a corresponding one of the end regions on the lower frame member, and the connectors enable the upper and the lower frame members to move between a closed position, in which the lens is securely engaged between the frame members, and an open position, in which the members are displaced from each other relative to the closed position and at least one of the frame members is free from engagement with the lens, thereby enabling the lens to be selectively removed and replaced.

21 Claims, 4 Drawing Sheets

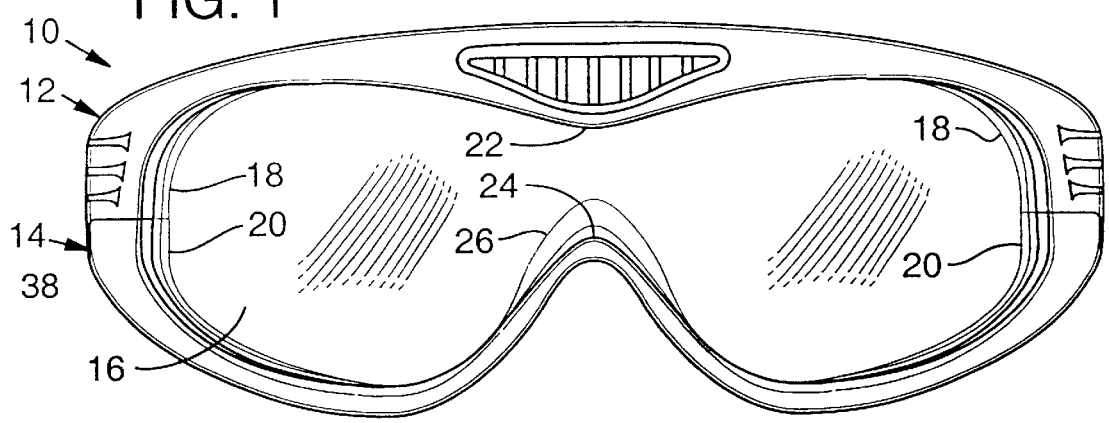
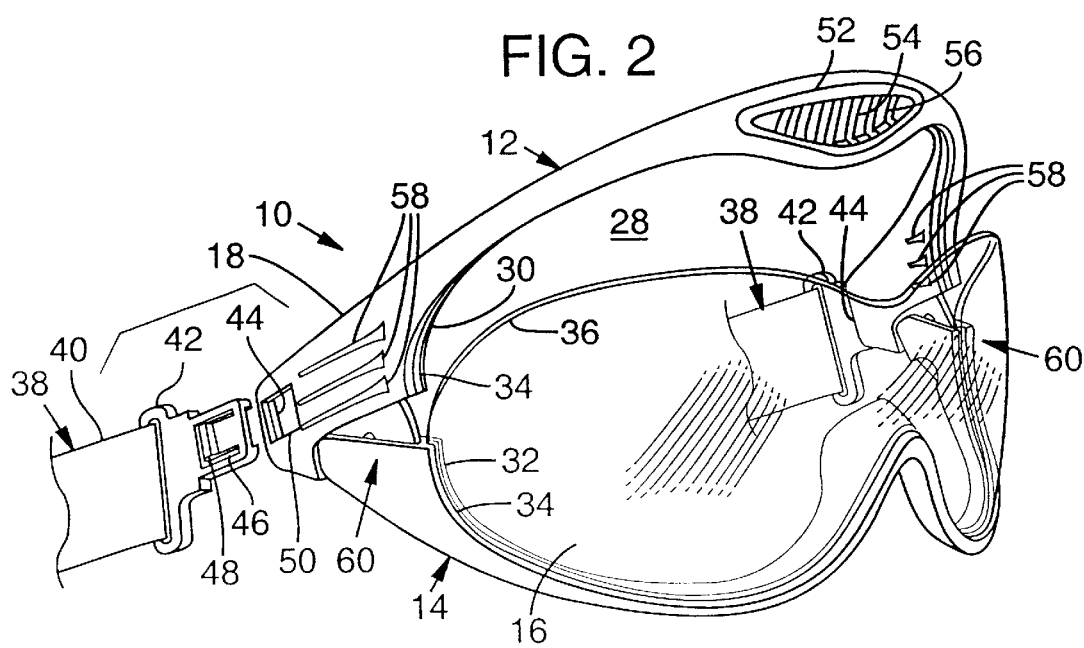
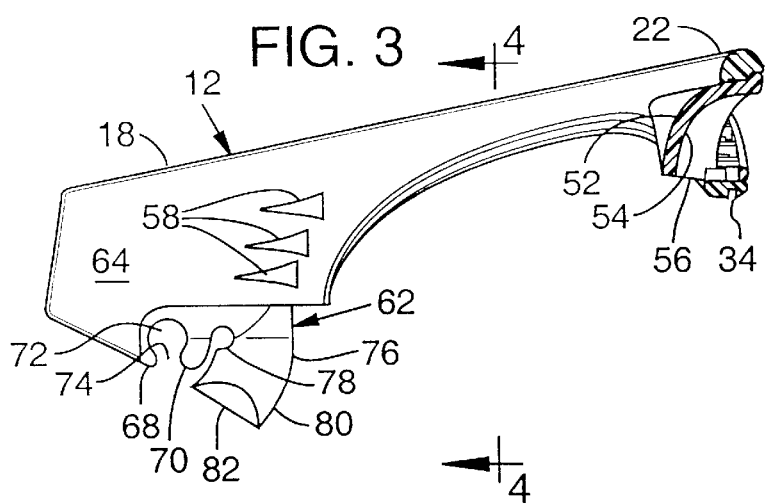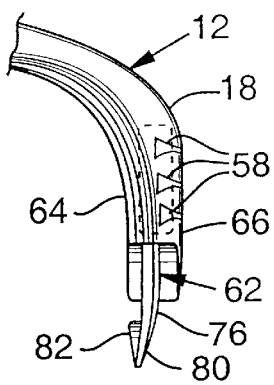

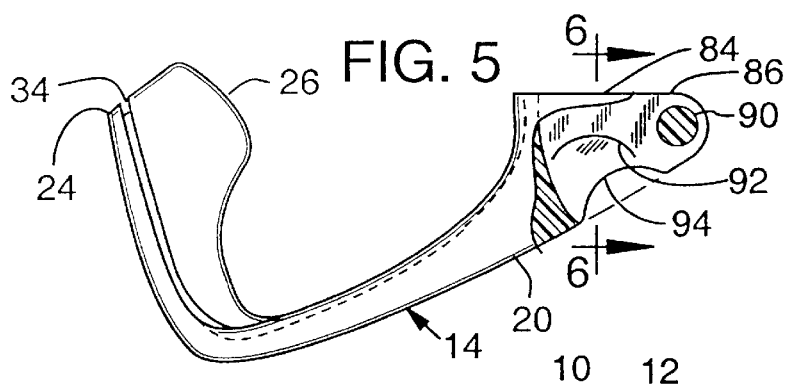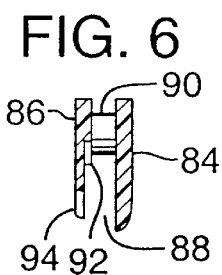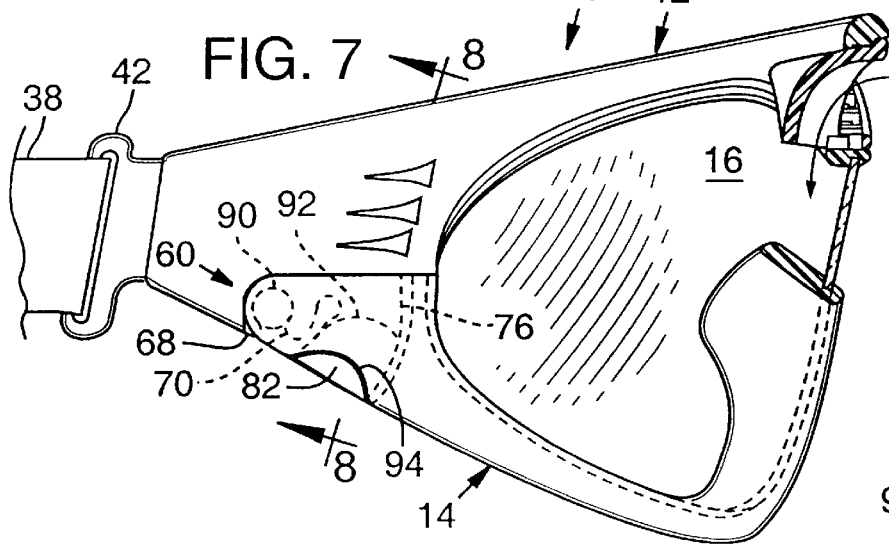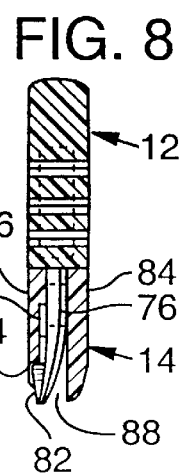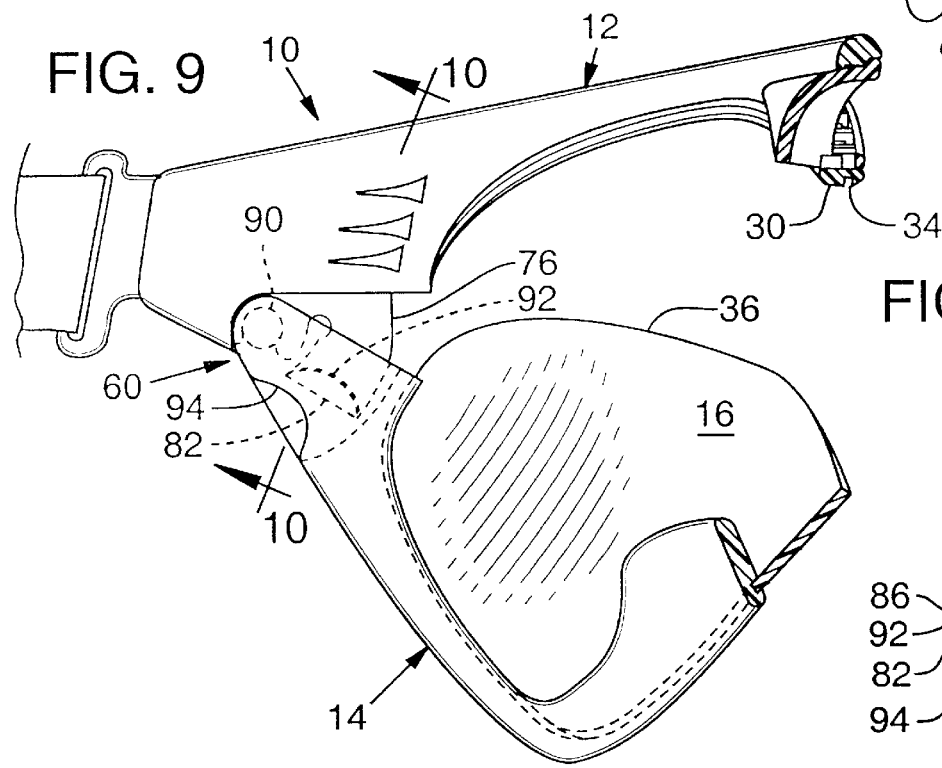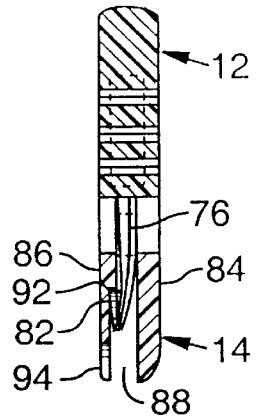

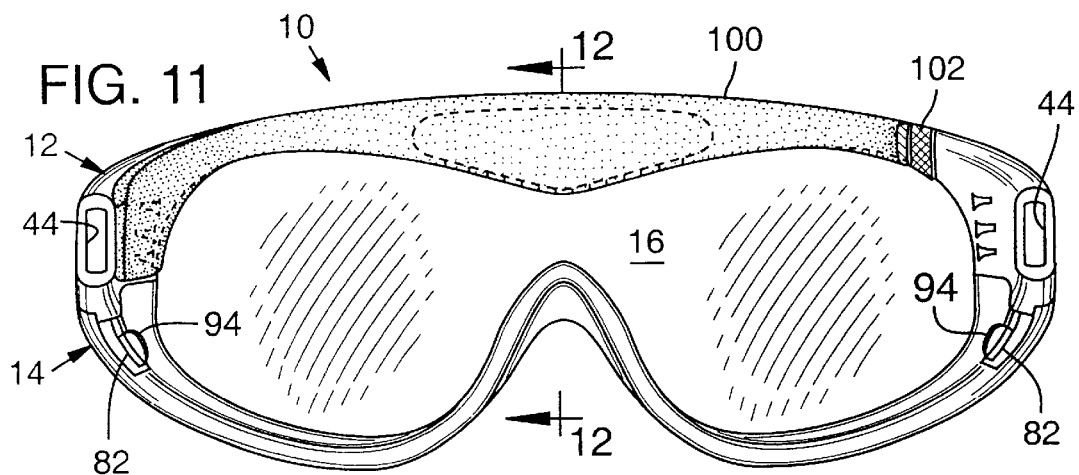
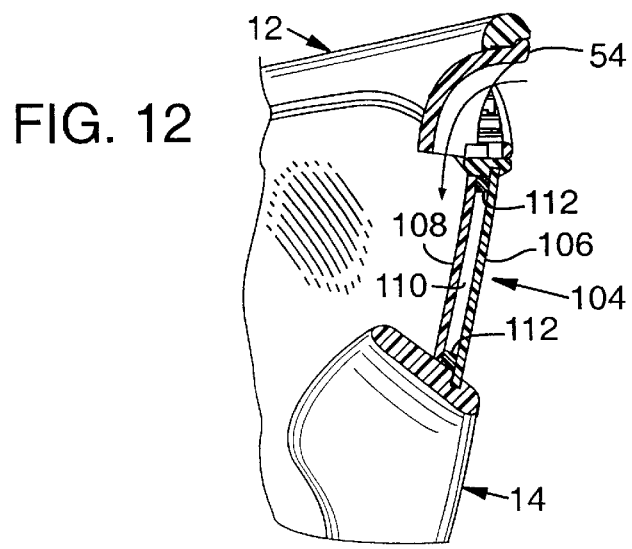
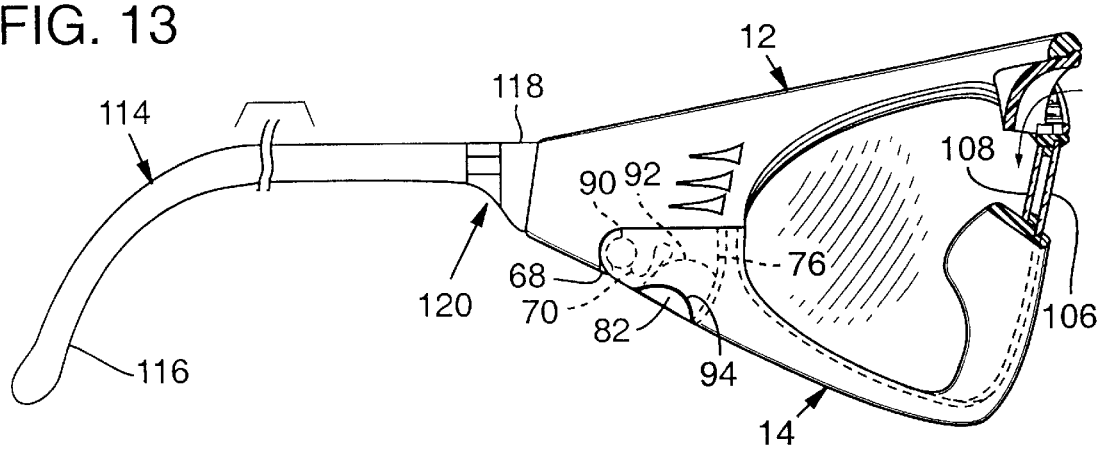

SKI GOGGLES WITH PIVOTAL FRAME MEMBERS FOR INTERCHANGING LENSES

FIELD OF THE INVENTION

The present invention relates generally to ski goggles, and more particularly to a pair of articulated ski goggles with pivotal upper and lower frame members that enable a lens to be selectively removed and replaced.

BACKGROUND AND SUMMARY OF THE INVENTION

Conventional ski goggles generally consist of a frame that is configured to be placed on a user's face in front of the user's eyes to protect and shield the user's eyes. The frame is usually a resilient, one-piece unit with a central aperture that defines the user's field of vision when the goggles are worn. A lens is mounted within the aperture and is seated in a spaced relationship with respect to the user's eyes. Ski goggles often include a layer of padding on the rear surface of the frame to cushion the engagement of the frame against the user's face, thereby making the goggles more comfortable to wear. An elastomeric strap or a pair of temple pieces are generally mounted on the rear of the frame adjacent each of the user's temples to provide a mechanism by which the goggles are retained on the user's head.

Although the frame and lens are generally constructed of an impact-resistant material, after continued use of the goggles it is often necessary to replace the lens. For example, the lens may be broken when the goggles are dropped, when the user falls while wearing the goggles, or when an object impacts the lens. In addition, even if the lens has not broken, it may become severely scratched and as a result may impair the user's vision.

Alternatively, it is often desirable for the lens to be interchangeable so that one of a variety of different lenses may be used, depending upon the conditions in which the goggles will be used and the user's preferences. For example, a user may prefer tinted lenses for sunny, bright days, but may opt for clear or yellow lenses on overcast or snowy days. Additionally, users with poor vision may desire a prescription lens so that they do not have to wear glasses or contacts in addition to the goggles.

Some conventional ski goggles do not allow the lens to be removed and replaced. Therefore, when the lens is damaged or broken, the goggles are no longer usable and must be discarded. In most conventional goggles, however, the frame is formed of a flexible, resilient material that is molded into the previously described configuration. To remove or replace the lens, the user must grasp the upper and lower portions of the frame and deform the frame by pulling the regions away from each other to expose the lens. Furthermore, the resilient nature of the frame requires the user to keep at least a portion of the frame displaced from its original position or else the frame will simply return to its original position, where it engages the entire periphery of the lens. This makes it difficult for a user to quickly remove and replace the lens. In addition, over time, the frame loses its resiliency, and therefore will not return completely to its original position. This results in the frame not forming a complete seal against the lens, which enables air, as well as snow and ice, to blow through the newly formed gap between the frame and lens and to irritate the user's eyes and face.

Furthermore, once the lens is removed, the resiliency of the frame makes it difficult to insert a new lens into the aperture in the frame. Specifically, while it may be fairly easy to insert a portion of the lens into the aperture, the user must stretch and flex the frame to get the lens completely within the aperture. This process often results in the user's fingers getting pinched between the lens and the frame.

Therefore, it is a principal object of the present invention to provide a pair of ski goggles with an articulated frame that enables a lens to be quickly and easily removed and replaced.

It is another object of the present invention to provide a pair of ski goggles with a frame that does not require constant pressure from the user to maintain the frame in an open position, whereby the lens may be selectively removed and replaced.

Yet another object of the present invention is to provide a pair of ski goggles that is economical to manufacture by virtue of having relatively few parts, featuring easily moldable components and not requiring precisely fitting parts.

Still another object of the present invention is to provide a pair of ski goggles that is rugged enough to withstand the abuses experienced in its operating environment.

Another object of the present invention is to provide a pair of ski goggles with upper and lower frame members that are moveable between a closed position, in which the frame members securely engage the lens, to an open position in which the frame members are displaced from each other relative to the closed position and wherein at least one of the frame members is free from engagement with the lens, thereby enabling the lens to be selectively removed and replaced.

The invention achieves these and other objects in the form of a pair of ski goggles having unitary upper and lower frame members that are each configured to extend substantially between a user's temples, and each include a pair of end regions. The upper and the lower frame members collectively define an aperture into which a lens is removably received, and the goggles further includes a pair of connectors. Each connector couples a respective one of the end regions on the upper frame member to a corresponding one of the end regions on the lower frame member, and the connectors enable the upper and the lower frame members to move between a closed position, in which the lens is securely engaged between the frame members, and an open position, in which the members are displaced from each other relative to the closed position and at least one of the frame members is free, or substantially free, from engagement with the lens, thereby enabling the lens to be selectively removed and replaced.

Many other features, advantages and additional objects of the present invention will become manifest to those versed in the art upon making reference to the detailed description which follows and the accompanying sheets of drawings in which preferred embodiments incorporating the principles of this invention are disclosed as illustrative examples only.

BRIEF DESCRIPTION OF THE DRAWINGS

FIG. 1 is a front elevational view of a pair of ski goggles constructed according to a preferred embodiment of the present invention.

FIG. 2 is an isometric view of the goggles shown in FIG. 1, with the upper and lower frame members pivoted to an open position, whereby the lens may be readily removed and replaced.

FIG. 3 is a fragmentary view of the inner surface of the right side of the upper frame member shown in FIG. 2.

FIG. 4 is a front elevational view of the portion of the upper frame member shown in FIG. 3, taken along line 4—4 in FIG. 3.

FIG. 5 is a fragmentary view of the outer surface of the right side of the lower frame member shown in FIG. 2 with a portion of the outer surface removed to show details of internal construction.

FIG. 6 is a front elevational view of the portion of the lower frame member shown in FIG. 5, taken along line 6—6 in FIG. 5.

FIG. 7 is a fragmentary view of the inner surface of the right side of the goggles shown in FIG. 2, with the upper and lower frame members in a closed position in which the upper and lower frame members securely engage the lens.

FIG. 8 is a front elevational view of the portion of the goggles shown in FIG. 7, taken along line 8—8 in FIG. 7.

FIG. 9 is a fragmentary view of the inner surface of the right side of the goggles shown in FIG. 2, with the upper and lower frame members shown in an open position in which the frame members are generally displaced from each other relative to the closed position and the upper frame member is free from engagement with the lens.

FIG. 10 is a front elevational view of the portion of the goggles shown in FIG. 9, taken along line 10—10 in FIG. 9.

FIG. 11 is a rear elevational view of the goggles shown in FIG. 1. As shown, the rear surface of the upper frame member includes a layer of padding material, a portion of which has been removed.

FIG. 12 is a cross-sectional view taken along line 12—12 in FIG. 11 and showing goggles with a dual lens unit.

FIG. 13 is a fragmentary view of the goggles shown in FIG. 12, in which the strap and clip shown in FIG. 7 have been replaced with a pivotal temple piece.

DETAILED DESCRIPTION OF THE PREFERRED EMBODIMENTS

Figure 14:
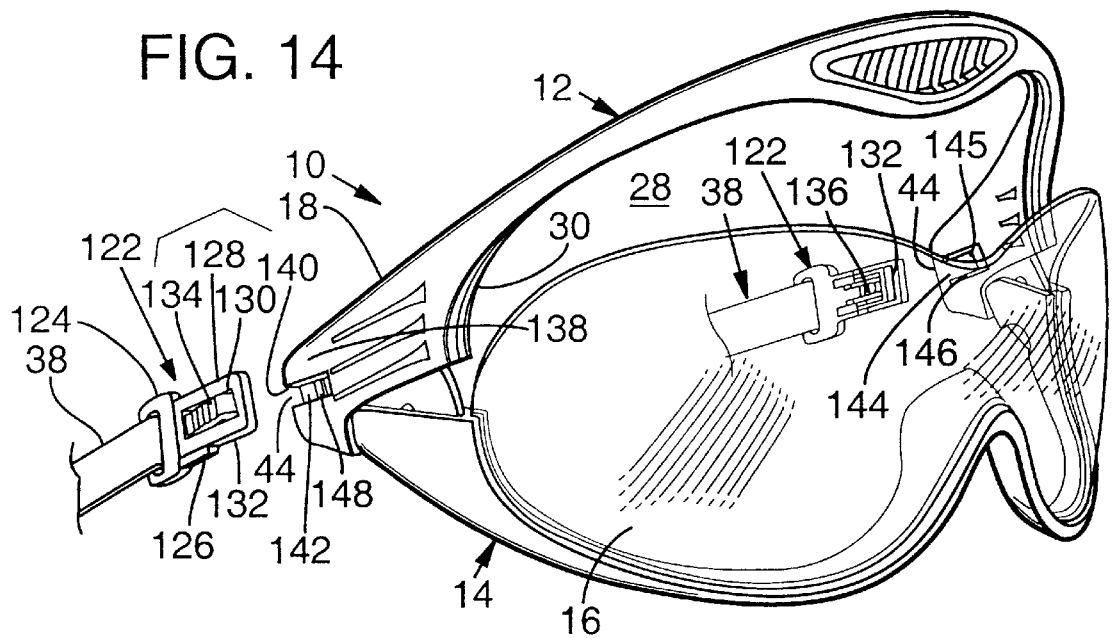
FIG. 14 is an isometric view of the goggles shown in FIG. 1, with each end region 18 adapted to removably receive an alternate embodiment of the clip connected to one of end regions of the goggles' strap.

A pair of ski goggles constructed in accordance with a preferred embodiment of the invention is shown in FIG. 1 and generally indicated at 10. Goggles 10 are configured to be placed on a user's face in front of the user's eyes to protect the user's face and eyes from such things as snow, ice, wind and cold when the goggles are worn by the user. Goggles 10 include a unitary upper frame member 12, a unitary lower frame member 14 and a lens 16. Each frame member 12 and 14 is constructed of a durable, impact-resistant material, such as polycarbonate, and has respective end regions 18 and 20 and a central portion 22 and 24. Central portion 24 of the lower frame member includes a nose piece 26, which extends generally upwardly and rearwardly to provide a surface shaped and configured to support the goggles on a user's nose when the goggles are worn.

As shown in FIG. 2, goggles 10 have a generally concave horizontal configuration and are shaped to extend between a user's temples and to conform generally to the shape of the user's face. Frame members 12 and 14 collectively define a generally arcuate aperture 28 therebetween into which lens 16 is seated and maintained in a spaced relationship in front of the user's eyes when the goggles are worn. The upper and lower frame members include generally opposed inner peripheries 30 and 32, respectively, which include channels 34 into which the outer periphery 36 of lens 16 is inserted and secured. As shown, lens 16 is a one-piece lens which is configured to extend in front of and protect both of a user's eyes. Lens 16 is constructed of an impact-resistant material, such as polycarbonate, and may be dipped, coated or otherwise treated to resist scratches. Furthermore, lens 16 may be tinted in any suitable shade or color and my be a prescription or other vision-enhancing lens.

Also shown in FIG. 2 is a strap 38 which includes end portions 40 that are coupled to a pair of clips 42. Clips 42 are each configured to be removably inserted into a respective one of a pair of rearward passages 44 in the upper frame member's end regions 18. The clips include an outwardly extending, deformable stop 46 with an elevated portion 48. Stop 46 enables a snap-fit with upper frame member 12 when clip 42 is inserted into a corresponding rearward passage on end region 18 and stop 46 projects outwardly from passage 44 and into lateral aperture 50. Once inserted and secured within the corresponding passage 44, clip 42 may be selectively removed by depressing or otherwise deforming stop 46 so that elevated portion 48 may be removed from the upper frame member through passage 44.

Upper frame member 12 includes a plurality of vents, which are shown in FIGS. 2 and 3. Central portion 22 includes a central vent 52 with a downwardly and rearwardly arched rearward portion 54 for directing airflow onto the inner surface of lens 16 and a plurality of baffles 56 for reducing cross-flow of air and channeling incoming air against rearward portion 54. The shape and curvature of rearward portion 54 prevents lens 16 from fogging due to pressure and temperature imbalances between the air on adjacent sides of the lens, and also protects the user's eyes from discomfort caused by the incoming, colder air by directing the air against the inner surface of lens 16 and away from the user's eyes. Central vent 52 is removably mounted on upper frame member 12, and it is intended to be within the scope of the present invention that vent 52 could be covered or removed and replaced with a stopper to prevent air from entering the goggles.

Additionally, each end region 18 on upper frame member 12 includes a plurality of vertically spaced lateral vents 58, which provide ventilation and equalize pressure and temperature between air outside of the goggles and the volume of air enclosed by the goggles when the goggles are worn. Each vent 58 extends through the corresponding end region of upper frame member 12, as shown in FIGS. 2 and 3, and further tapers rearwardly and inwardly from generally adjacent aperture 28 to generally adjacent lateral aperture 50. When the goggles are worn by a user, air that enters through central vent 52 will generally exit the pocket defined between the goggles and the user's face by passing through lateral vents 58.

As shown in FIG. 2, upper and lower frame members 12 and 14 are pivotally coupled together by a pair of connectors 60. Specifically, each end region 18 on upper frame member 12 is pivotally connected to the corresponding end region 20 on lower frame member 14. Connectors 60 enable the upper and lower frame members to pivot about an axis extending through the connectors and between defined orientations that include an open position and a closed position, as discussed below. As shown, frame members 12 and 14 are in an open position, in which members 12 and 14 are displaced from each other relative to the closed position shown in FIG. 1, in which lens 16 is securely engaged between the frame members. As shown in FIG. 2, central portions 22 and 24 are displaced from each other relative to the closed position, and upper frame member 12 is free from engagement with lens 16, thereby enabling the lens to be selectively removed and replaced. It should be understood that it is meant to be within the scope of the present invention that the open position includes either of the frame members being free, or substantially free, from engagement with lens 16.

One of the upper frame member's end regions 18 is shown in FIGS. 3 and 4. It should be understood that upper frame member 12 is symmetrical, and that the other end region 18 has the same shape, configuration and components as the end region shown in FIGS. 3 and 4. End region 18 includes a downwardly projecting member 62, which forms a portion of connector 60. Specifically, each connector 60 includes a downwardly projecting member 62 on end region 18 and a second portion on the corresponding end region 20 on lower frame member 14, which is described subsequently. The portions collectively couple upper and lower frame members 12 and 14 together and enable the members to be selectively pivoted and retained between a range of defined positions bounded by the previously described closed and open positions.

As shown in FIGS. 3 and 4, projecting member 62 extends generally downwardly from end region 18 between the inner and outer surfaces or walls 64 and 66 of end region 18. Projecting member 62 includes a pair of arcuate members 68 and 70, which collectively define a generally circular cavity 72 with an opening 74. Member 62 further includes a latch mechanism 76 spaced forwardly from arcuate member 70. Mechanism 76 includes a notched or relieved portion 78 adjacent member 70 that enables mechanism 76 to flex or otherwise move independent of the rest of member 62. As shown in FIGS. 3 and 4, latch mechanism 76 has an arcuate configuration, with a lower region 80 that extends generally inwardly and rearwardly relative to the rest of mechanism 76. Lower region 80 includes a tab 82, which is shown with a generally semicircular configuration. Tab 82 extends upwardly and inwardly from lower region 80 and is configured to sequentially and selectively engage a plurality of stops on the corresponding end region 20 of lower frame member 14 to thereby enable the frame members to be selectively retained in and pivoted between a plurality of defined positions with respect to each other.

One of the jaw-like lower frame member's end regions 20 is shown in FIGS. 5 and 6. Specifically, FIGS. 5 and 6 show the end region which corresponds with the upper frame member's end region 18 shown in FIGS. 3 and 4. Similar to end regions 18 on the upper frame member, the lower frame member's end regions 20 are symmetrical and each should contain the same elements and sub-elements.

End region 20 includes rearward outer and inner walls or surfaces 84 and 86, which are shown in FIGS. 5 and 6. Walls 84 and 86 collectively define a slot 88 therebetween, which is sized and shaped to receive downwardly projecting portion 62 on end region 18. A spacer 90, which as shown has a generally cylindrical configuration, extends between the rearward portions of walls 84 and 86 and is sized and positioned to be inserted into cavity 78 through opening 80 and pivotally retained within cavity 78 by members 68 and 70 in a snap-fit relationship.

Also shown in FIGS. 5 and 6 are a pair of stops 92 and 94, which are integrally formed on inner wall 86. Stops 92 and 94 are configured to correspond to the shape of tab 82 as it travels along the radial path when the upper and lower frame members pivot with respect to each other, such as the previously discussed closed and open positions. The stops define positions at which the upper and lower frame members are maintained with respect to each other. As shown, stop 92 defines the goggles' open position, shown in FIG. 2. Stop 94 is positioned radially downwardly and interiorly of stop 92 and defines the goggles' closed position, which is shown in FIG. 1.

FIGS. 7 and 8 are fragmentary views showing the right portion of goggles 10 in the closed position. As shown, spacer 90 is pivotally mounted between arcuate members 68 and 70, thereby pivotally connecting upper and lower frame members 12 and 14. Downwardly projecting member 76 is received within slot 88, between the outer and inner surfaces 84 and 86 of lower frame member 14, and tab 82 engages stop 94 to retain the frame members in the closed position, whereby lens 16 is secured between the frame members.

FIGS. 9 and 10 generally correspond to FIGS. 7 and 8, except the frame members have then pivoted to their open position. As shown, tab 82 engages stop 92 instead of stop 94, and lens 16 is no longer engaged by upper frame member 12 and may be selectively removed and replaced from the goggles.

To adjust the goggles from the closed position shown in FIGS. 7 and 8 to the open position shown in FIGS. 9 and 10, the tabs 82 on each of the upper frame member's downwardly projecting members 76 must be deformed or pressed outwardly toward the lower frame member's outer wall 84 until the tabs no longer engage stop 94. At this point, the frame members may be pivoted away from each other. As the upper and lower frame members move apart from each other, spacer 90 rotates within the cavity 72 defined by arcuate members 68 and 70, lens 16 is at least partially disengaged by upper frame member 12, and tab 82 is translated upwardly along the lower frame member's inner surface 86 toward stop 92. Because tab 82 has been deformed from its resting position, tab 82 is urged or biased against the lower frame member's inner wall 86. Preferably, the force of tab 82 acting on wall 86 is sufficient to at least temporarily maintain the upper and lower frame members in an intermediate position between the closed and open positions. This enables a user to control the degree of displacement between the upper and lower frame members and precludes the user from having to maintain constant pressure on the frame members to maintain them in a particular orientation with respect to each other. As the frame members are displaced further away from each other, tab 82 engages stop 92, and the displacement of the frame members away from each other is completed. To return the goggles to the closed position, the upper and lower frame members are pivoted back together until tab 82 engages stop 94.

Because tabs 82 are operatively positioned on the inner surface of the goggles, they can be easily depressed by a user's thumbs or index fingers while the user is holding the goggles. As such, tabs 82 may also be referred to as a user-manipulable element.

It should be further understood that it is meant to be within the scope of the present invention that the goggles may be pivoted between the open and closed positions without requiring the user to manually depress the tabs. For example, tabs 82 or stops 94 may be configured to constrain the pivotal movement of the frame members away from each other until a sufficient force is applied to urge the frame members apart from each other. In this configuration, tabs 82 or stops 94 may include a chamfer or relieved portion which causes tabs 82 to disengage stops 94 once this sufficient amount of force is applied. The required amount of force should be selected so that normal jostling and shaking of the goggles as they are worn and used would not cause tabs 82 to disengage stops 94.

FIG. 11 is a rear view showing goggles 10 in their closed position. As shown, tabs 82 engage stops 94, and lens 16 is securely received and engaged by the upper and lower frame members 12 and 14, respectively. Also shown in FIG. 11 is a pad 100 which is formed of a resilient material for cushioning the engagement of the goggles against the user's face. As shown, pad 100 substantially covers the inner surface of upper frame member 12, however, it should be understood that other configurations and placements of pads may be used. Furthermore, as shown in FIG. 11, pad 100 is secured to upper portion 12 by a hook and loop closure mechanism 102 which enables pad 100 to be selectively removed and replaced from the goggles. This is advantageous if pad 100 wears out or becomes wet, or if a user wants to use a different shape, thickness, or type of pad. It should be understood, however, that pad 100 may be secured to goggles 10 by any suitable form of attachment, such as an adhesive.

In FIG. 12, an alternate embodiment of lens 16 is indicated generally at 104. As shown, lens 104 includes an outer lens 106, which is similar in shape and configuration to previously described lens 16, and an inner lens 108, which is formed of cellulose propionate or another suitable material and which is disposed inwardly from outer lens 106. Lenses 106 and 108 collectively define an insulating layer or thermal barrier 110. As shown, barrier 110 is an air-filled pocket which reduces the likelihood of lens 104 fogging or otherwise obscuring a user's vision due to pressure and temperature imbalances between the air on either sides of the goggles, and further protect the user's eyes and face from irritation and discomfort caused by the cold environment in which the goggles are commonly used. Lenses 106 and 108 are maintained in a spaced relationship with each other by spacers 112, which are preferably formed of a polyethylene blend or other suitable composition and extend around the entire perimeter of inner lens 108 to adhere the lenses together and enclose thermal barrier 110. As shown, the upper and lower frame members 12 and 14 engage both the inner and the outer lenses.

FIG. 13 is a fragmentary side view of the goggles, similar to the view shown in FIG. 7, only in which strap 38 and clip 42 have been replaced with a pivotal temple piece 114. Piece 114 includes a rearward portion 116 which is configured to wrap at least partially around a user's ear, and thereby support the goggles on the user's face. As shown, temple piece 114 includes a forward portion 118, which is configured to be removably inserted through one of the previously discussed rearward passages 44, similar to clip 42. Forward and rearward portions 118 and 116 are connected attached by a conventional hinge mechanism 114 to enable the temple pieces to be folded against goggles 10 when not in use.

Figure 15:
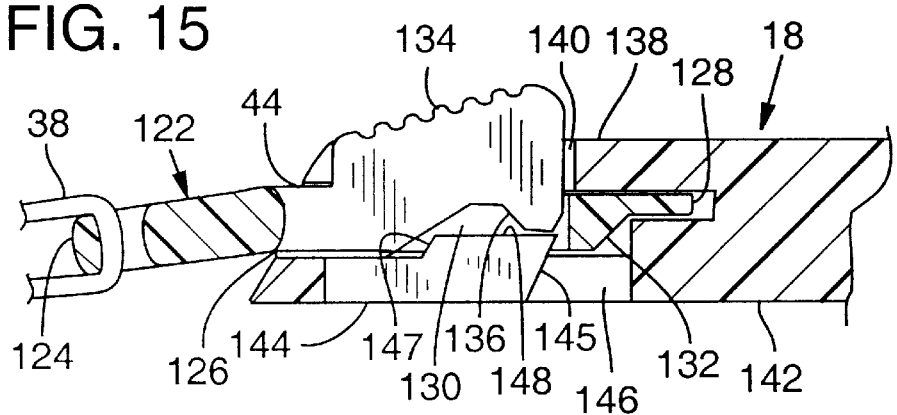
FIG. 15 is an enlarged cross-sectional view of the clip and end region shown in FIG. 14, with the clip secured within the upper frame member's end region.
Figure 16:
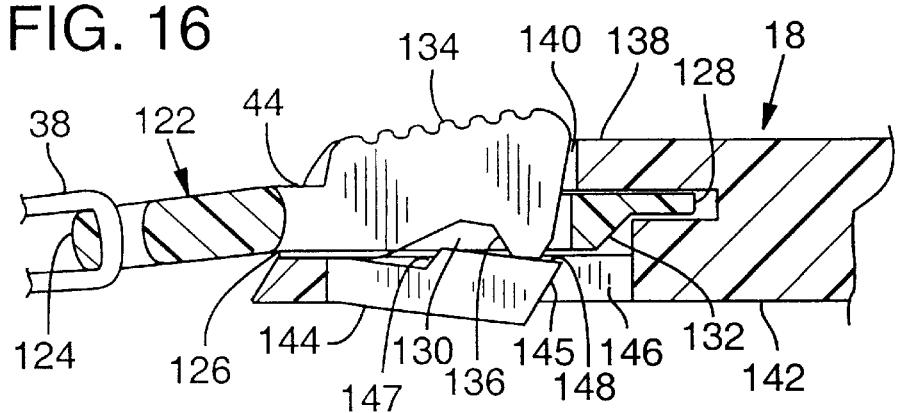
FIG. 16 shows the clip and end region shown in FIG. 15, with the tab on the clip depressed to enable the clip to be removed from the upper frame member's end region.

In FIGS. 14–16, the previously described ski goggles are shown with an alternate embodiment of clip 42, which is indicated generally at 122. Clip 122 operates on a snap-lock mechanism, with a rearward portion 124 that receives strap 38 and a forward region 126 that includes a generally box-like member 128, which is configured to be received within aperture 44 in the rear portion of the upper frame member's end region 18. Member 128 defines a hollow central portion 130 and includes an inclined front wall 132, which cooperate to enable the clip to be selectively secured within and removed from end region 18. Member 128 further includes an outwardly extending tab 134 that extends generally transverse to member 128 and includes a downwardly extending front portion 136 normally disposed partially within hollow central portion 130 formed by box-like member 128.

As shown in FIG. 14, the outer surface 138 of the upper frame member's end region 18 defines an elongate passage 140 through which tab 134 may slide. Furthermore, the inner surface 142 of end region 18 includes a resilient member 144, which is integrally formed with surface 142 and configured to flex inwardly from a position generally adjacent the rearward portion of end region 18. As shown, the forward, upper and lower sides of member 144 are separated from the rest of inner surface 142 by a cut-out or slot 146. Member 144 includes inclined front and rear walls 145 and 147, respectively, as well as an outwardly projecting stop 148, which extends within aperture 44 toward outer surface 138. As shown, aperture 44 and passage 140 collectively define a generally T-shaped track or channel through which at least a portion of clip 122 is selectively inserted and removed.

When clip 122 is inserted into the track, the frame member's inclined front wall 132 engages rear wall 147 of stop 148 and causes member 144 to deform inwardly to allow front wall 132 to pass over stop 148. Once front wall 132 has completely passed over stop 148, member 144 returns to its original position, and clip 122 is therefore retained within the tract on account of the snap-fit between member 144 and stop 148, as shown in FIG. 15. As shown, downwardly extending portion 136 of tab 134 is positioned above stop 148.

To remove clip 122, the user simply presses tab 134 inwardly, in the direction of stop 148, to cause the tab's downwardly extending front portion 136 to engage stop 148 and thereby cause member 144 of end region 18 to deform inwardly so that front wall 132 may be passed over stop 148, as shown in FIG. 16. Once front wall 132 is passed rearwardly over stop 148, tab 134 is released and member 144 returns to its original, unstressed position.

While the present invention has been shown and described with reference to the foregoing preferred embodiment, it should be understood by those of skill in the art that other changes in form and detail may be made therein without departing from the spirit and scope of the invention as defined in the appending claims.

I claim:

1. Ski goggles, comprising:
   a unitary upper frame member configured to extend substantially between a user's temples, the upper frame member including a pair of end regions;
   a unitary lower frame member configured to extend substantially between the user's temples, the lower frame member including a pair of end regions, wherein the upper and the lower frame members collectively define an aperture into which a lens is removably received; and
   a pair of connectors, each connector coupling a respective one of the end regions on the upper frame member to a corresponding one of the end regions on the lower frame member, wherein the connectors maintain the connection between the end regions of the frame members while enabling the members to move between a closed position in which the lens is seated between the frame members, and an open position in which the members are moved at least partially apart from each other so that one of the frame members disengages the lens, thereby enabling the lens to be selectively removed and replaced.

2. The goggles of claim 1, wherein the connectors enable the members to pivot between the closed and the open positions.

3. The goggles of claim 1, wherein the lens includes an outer periphery, and the upper and the lower frame members include inner peripheries defining an elongate channel into which at least a portion of the outer periphery of the lens is seated.

4. The goggles of claim 1, wherein the end regions of the upper and the lower frame members include latch mechanisms that cooperate to selectively and releasably retain the upper and the lower frame members in defined orientations with respect to each other.

5. The goggles of claim 4, wherein the latch mechanism includes a user-manipulable element for releasing the upper and the lower frame members from a defined orientation and enabling the members to be moved to another defined orientation.

6. The goggles of claim 4, wherein the defined orientations include a closed position, in which the lens is securely engaged between the frame members, and an open position, in which the members are displaced from each other relative to the closed position and at least one of the frame members is free from engagement with the lens.

7. The goggles of claim 1, wherein each end region on the lower frame member includes a slot, wherein each end region on the upper frame member includes a projecting member that is received into the slot in the corresponding end region on the lower frame member, and wherein each end region on the lower frame member further includes plural stops extending within the slot to selectively and releasably engage the projecting member and thereby, selectively and releasably retain the upper and the lower frame members in defined orientations with respect to each other.

8. The goggles of claim 7, wherein the projecting member includes a tab extending from the projecting member to selectively and sequentially engage the stops.

9. The goggles of claim 8, wherein the tab includes a user-manipulable element.

10. The goggles of claim 1, wherein the lens has an inner surface oriented toward a user's eyes when the goggles are worn by the user, and wherein the upper frame member includes a vent configured to direct airflow from external the goggles through the upper frame member and directly onto the inner surface of the lens.

11. Ski goggles, comprising:
an upper frame member with generally opposed end regions;
a jaw-like lower frame member with generally opposed end regions; and
a pair of connectors, each connector coupling a respective one of the end regions on the upper frame member with a corresponding end region on the lower frame member, wherein the upper and the lower frame members collectively define an aperture into which a lens is removably received, and further wherein the connectors maintain the connection between the end regions of the frame members while enabling the frame members to be selectively moved between a closed position, wherein the frame members each securely engage the lens, and an open position, wherein the frame members are displaced from each other relative to the closed position and at least one of the frame members is free from engagement with the lens, thereby enabling the lens to be selectively removed and replaced.

12. The goggles of claim 11, wherein the connectors enable pivotal movement of the frame members with respect to each other.

13. The goggles of claim 11, wherein the lens includes an outer periphery, and the upper and the lower frame members include inner peripheries defining an elongate channel into which the outer periphery of the lens is seated.

14. The goggles of claim 11, wherein the end regions of the upper and the lower frame members include latch mechanisms that cooperate to selectively and releasably retain the upper and the lower frame members in defined orientations with respect to each other.

15. The goggles of claim 14, wherein the latch mechanism includes a user-manipulable element for releasing the upper and the lower frame members from a defined orientation and enabling the members to be moved to another defined orientation.

16. The goggles of claim 14, wherein the defined orientations include the closed position and the open position.

17. The goggles of claim 11, wherein each end region on the lower frame member includes a slot, wherein each end region on the upper frame member includes a projecting member that is received into the slot in the corresponding end region on the lower frame member, and wherein each end region on the lower frame member further includes plural stops extending within the slot to selectively and releasably engage the projecting member and thereby, selectively and releasably retain the upper and the lower frame members in defined orientations with respect to each other.

18. The goggles of claim 17, wherein the projecting member includes a tab extending from the projecting member to selectively and sequentially engage the stops.

19. The goggles of claim 18, wherein the tab includes a user manipulable element.

20. The goggles of claim 11, wherein the lens has an inner surface oriented toward a user's eyes when the goggles are worn by the user, and wherein the upper frame member includes a vent configured to direct airflow from external the goggles through the upper frame member and directly onto the inner surface of the lens.

21. Ski goggles, comprising:
an upper frame member with a central portion and opposed end regions;
a lower frame member with a central portion and opposed end regions; and
a pair of connectors coupling each of the end regions of the upper frame member with a respective one of the end regions of the lower frame member, wherein the upper and the lower frame members collectively define an aperture into which a lens is removably received, and further wherein the connectors enable the upper and the lower frame members to be selectively pivoted about an axis extending through the connectors between a closed position, in which the lens is securely engaged between the frame members, and an open position, in which the central portions of the frame members are displaced from each other relative to the closed position and at least one of the frame members is free from engagement with the lens, thereby enabling the lens to be selectively removed and replaced.

* * * * *